(12) United States Patent
Bruning et al.

(10) Patent No.: US 9,622,944 B2
(45) Date of Patent: Apr. 18, 2017

(54) GEL-WIPE FOR PERSONAL CARE AND HOUSEHOLD CLEANSING

(71) Applicant: JOHNSON & JOHNSON CONSUMER INC., Skillman, NJ (US)

(72) Inventors: Elizabeth Bruning, Somerset, NJ (US); Gabriella Marie DeMarco, Basking Ridge, NJ (US); Euen Thomas Graham Ekman Gunn, Hopewell, NJ (US); Claudia Kaminski, Milford, NJ (US); Kevin Lahey, South Plainfield, NJ (US); Prithwiraj Maitra, Hillsborough, NJ (US); Selina Moses, Plainsboro, NJ (US); Delores Santora, Ringoes, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 576 days.

(21) Appl. No.: 14/134,123

(22) Filed: Dec. 19, 2013

(65) Prior Publication Data
US 2015/0174014 A1 Jun. 25, 2015

(51) Int. Cl.
*A61K 8/02* (2006.01)
*A47L 13/17* (2006.01)
(Continued)

(52) U.S. Cl.
CPC ............ *A61K 8/0208* (2013.01); *A47L 13/17* (2013.01); *A61K 8/027* (2013.01); *A61K 8/8147* (2013.01);
(Continued)

(58) Field of Classification Search
CPC ...... A47L 13/17; D06M 11/38; D06M 15/263; D06M 2400/02; D04H 3/00;
(Continued)

(56) References Cited

U.S. PATENT DOCUMENTS

| | | |
|---|---|---|
| 4,366,206 A | 12/1982 | Tanaka |
| 4,374,175 A | 2/1983 | Tanaka |

(Continued)

FOREIGN PATENT DOCUMENTS

JP 2000143484 A 5/2000

OTHER PUBLICATIONS

International search report dated Jul. 22, 2016, for corresponding international application PCT/US2016/031406.
(Continued)

*Primary Examiner* — Jeremy R Pierce

(57) ABSTRACT

Gel-wipes suitable for use in personal care and household cleansing applications are disclosed, which include a substrate having a first surface, a second surface opposing the first surface and a body disposed between and defined by the first and second surfaces, fibers having an outer surface and an inner core, a polymeric gel distributed throughout the substrate such that a substantial portion of the fibers contain the polymeric gel distributed throughout the inner core of the fibers; and a liquid cleansing composition, wherein the inner core of a substantial portion of the fibers and the polymeric gel are substantially free of the liquid cleansing composition; as well as methods of making the gel-wipe.

17 Claims, 4 Drawing Sheets

(51) Int. Cl.
*A61Q 19/10* (2006.01)
*C11D 17/04* (2006.01)
*A61Q 19/00* (2006.01)
*A61K 8/81* (2006.01)
*D06M 11/38* (2006.01)
*D06M 15/263* (2006.01)

(52) U.S. Cl.
CPC ............ *A61Q 19/00* (2013.01); *A61Q 19/10* (2013.01); *C11D 17/049* (2013.01); *D06M 11/38* (2013.01); *D06M 15/263* (2013.01); *D06M 2400/02* (2013.01)

(58) Field of Classification Search
CPC .. C11D 17/049; A61K 8/0208; A61K 8/8147; A61K 8/027; A61Q 19/10; A61Q 19/00
See application file for complete search history.

(56) References Cited

U.S. PATENT DOCUMENTS

| | | |
|---|---|---|
| 4,507,204 A | 3/1985 | Tanaka et al. |
| 4,731,067 A | 3/1988 | Le-Khac |
| 4,743,244 A | 5/1988 | Le-Khac |
| 4,813,945 A | 3/1989 | Le-Khac |
| 4,873,143 A | 10/1989 | Tanaka |
| 4,880,868 A | 11/1989 | Le-Khac |
| 4,892,533 A | 1/1990 | Le-Khac |
| 5,026,784 A | 6/1991 | Le-Khac |
| 5,079,004 A * | 1/1992 | Blank .................... A01N 25/10 424/404 |
| 5,079,080 A | 1/1992 | Schwarz |
| 5,079,306 A | 1/1992 | Le-Khac |
| 5,409,771 A | 4/1995 | Dahmen et al. |
| 5,466,731 A | 11/1995 | Akers et al. |
| 5,607,550 A | 3/1997 | Akers |
| 5,652,049 A * | 7/1997 | Suzuki .................... B32B 5/26 428/206 |
| 6,413,747 B1 | 7/2002 | Kato et al. |
| 6,992,054 B2 | 1/2006 | Lee et al. |
| 7,105,177 B1 * | 9/2006 | Barney ................ A61K 8/0208 424/402 |
| 7,718,249 B2 | 5/2010 | Russell et al. |
| 8,440,606 B2 | 5/2013 | Mundschau et al. |
| 8,906,839 B2 | 12/2014 | Lentsch et al. |
| 8,940,680 B2 | 1/2015 | Bernard et al. |
| 2004/0185730 A1 | 9/2004 | Lambino et al. |
| 2005/0159063 A1 | 7/2005 | Hill et al. |
| 2009/0018047 A1 | 1/2009 | Mundschau et al. |
| 2009/0081269 A1 | 3/2009 | Erazo-Majewicz et al. |
| 2010/0000116 A1 | 1/2010 | Aouad et al. |
| 2012/0121671 A1 | 5/2012 | Goldstein |
| 2015/0174014 A1 | 6/2015 | Bruning et al. |

OTHER PUBLICATIONS

International search report dated Apr. 2, 2015, for corresponding international application PCT/US2014/069491.

* cited by examiner

GEL-WIPE FOR PERSONAL CARE AND HOUSEHOLD CLEANSING

FIELD OF THE INVENTION

The present invention relates to a fibrous gel-wipe suitable for use in personal care and household cleansing applications, which gel-wipe includes a polymeric gel and a liquid cleansing composition.

BACKGROUND OF THE INVENTION

Fibrous substrates, e.g. wipes, are known for use in personal care and household cleansing applications. Certain of the known wipes are dry, i.e., they do not include any liquid composition, cleansing or otherwise, impregnated onto or into the fibrous substrate. Other fibrous wipes do include liquid cleansing compositions impregnated onto the fibrous substrate and are referred to herein as wet wipes. Such cleansing compositions may include lathering surfactants and other ingredients for imparting cleansing or other desired properties to the wet wipe. One of the issues with such wet wipes is that the liquid composition may migrate from the fibrous substrate over time, resulting in decreased cleaning efficiency and waste of the cleansing composition.

To address the issue of migration of the liquid cleansing compositions from known wet wipes, certain gel-wipes for use in personal care and household cleansing applications have been disclosed. In some embodiments, such gel-wipes have a liquid portion that includes a thickening or gelling polymer and a thickening or gelling agent. The liquid portion containing the gelling polymer and the gelling agent is then impregnated in the fibrous substrate. In other embodiments, a gelling agent is incorporated into the substrate, followed by application of a liquid portion that contains the gelling polymer to the substrate having the impregnated gelling agent. In both embodiments, due to formation of the gel by the gelling polymer and gelling agent in the presence of the liquid portion, which includes any cleansing agents contained therein, a polymeric gel containing the liquid portion distributed there through is distributed throughout the substrate, including throughout the body or core of the fibers forming the substrate.

While such known gel-wipes are purported to reduce the migration of liquid from the wet-wipes, certain issues still exist with such gel-wipes. For example, as the substrate is entirely impregnated with the polymeric gel containing the cleansing liquid portion, a portion of the cleansing solution will be "bound" within the core body of the fibers where it will provide no cleansing benefit. Additionally, such gel-wipes may use more cleansing liquid portion than is necessary, resulting in waste of cleansing solutions.

It would be advantageous for one to develop a gel-wipe that not only provides as good as or better cleansing efficacy than gel-wipes described above, but that also avoids issues such as fluid migration of known wet wipes as described above. The inventions claimed herein provide such gel-wipes that not only are more efficacious in cleansing compared to known gel-wipes, but also utilize less cleansing solution to achieve efficient cleansing.

SUMMARY OF THE INVENTION

The present invention includes a gel-wipe suitable for use in personal care and household cleansing applications. The gel-wipe includes a substrate comprising fibers having an outer surface and an inner core. The substrate has a first surface, a second surface opposing the first surface, and a body disposed between and defined by the first and second surfaces. The body of the substrate comprises fiber that is located between the first and second surfaces of the substrate, in addition to the spaces between the fibers, i.e. the interstitial spaces of the substrate body. A polymeric gel is distributed throughout the substrate such that a substantial portion of the fibers comprise the polymeric gel distributed throughout the inner core of the fibers. The gel-wipe also includes a liquid cleansing composition, wherein the inner core of the fibers and the polymeric gel are substantially free of the liquid cleansing composition. The invention also includes methods of making the gel-wipe comprising the ordered steps of providing a substrate comprising fibers having an outer surface and an inner core, where the substrate includes a first surface, a second surface opposing the first surface, and a body disposed between and defined by the first and second surfaces; contacting the substrate with a liquid composition having a gelling polymer dissolved therein, under conditions effective to distribute the liquid composition on the first and second surfaces and throughout the body of the substrate, and throughout the inner core of a substantial portion of the fibers; contacting the substrate comprising the gelling polymer distributed there through with a gelling agent capable of reacting with the gelling polymer, thereby forming a polymeric gel distributed throughout the substrate, and throughout the inner core of a substantial portion of the fibers; and contacting the substrate comprising the polymeric gel distributed there through with a liquid cleansing composition, whereby the inner core of the fibers containing the polymeric gel distributed there through are substantially free of the liquid cleansing composition.

DETAILED DESCRIPTION OF THE FIGURES

DETAILED DESCRIPTION OF THE INVENTION

Figure 1:
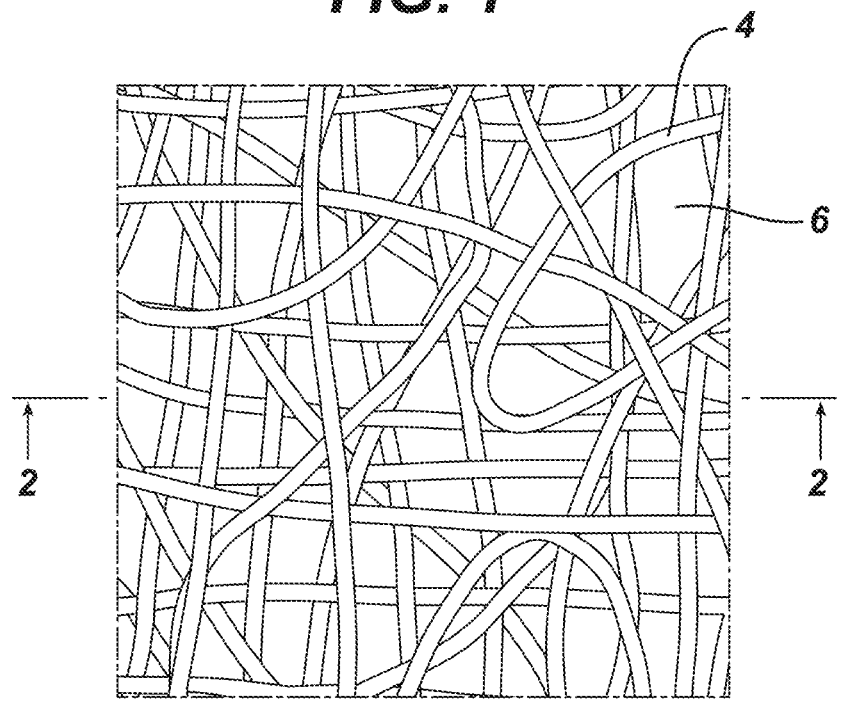
FIG. 1 is a top view of a fibrous substrate used in gel-wipes according to the present invention.

As used herein, the term "wet-wipe" refers to a fibrous substrate of woven, non-woven or knitted fabric which, during its manufacture, has a liquid cleansing composition, as defined herein, applied thereto, so that the liquid cleansing composition can be retained on the fibrous substrate where it is available for cleansing upon utilization by a consumer.

As used herein, the term "gel-wipe" refers to a fibrous substrate of woven, non-woven or knitted fabric which, during its manufacture, has a liquid cleansing composition and a polymeric gel, as defined herein, applied thereto, so that the liquid cleansing composition can be retained on the fibrous substrate where it is available for cleansing upon utilization by a consumer.

By "substantially free of liquid cleansing composition", it is meant that the fiber core and the polymeric gel in gel-wipes of the present invention do not contain a liquid cleansing composition in an amount effective to improve cleansing efficacy as described herein, compared to a fiber core or polymeric gel that does not contain any such liquid cleansing composition. Although not intending to be limited by the following, it is noted that increased cleansing efficacy of the gel-wipes of the present invention may be characterized, on one hand, as an improvement, or increase, in actual cleansing performance, compared to prior art gel-wipes, when comparable amounts of the same or similar cleansing compositions are used in the prior art and inventive gel-wipes, as claimed. Furthermore, increased cleansing efficacy may be realized where comparable cleansing efficacy of prior art gel-wipes and inventive gel-wipes is achieved, and where the inventive gel-wipe utilizes significantly reduced levels of liquid cleansing composition to achieve the comparable results.

Substrates useful in the present invention are typically produced from cellulosic pulp and/or man-made fibers having an outer surface and an inner core. The substrates are selected to provide the necessary properties for the particular end use application and are to be considered disposable and/or biodegradable in nature. The body of the substrate comprises fibers that are located between the first and second surfaces of the substrate, in addition to the spaces between the fibers, i.e. the interstitial spaces of the substrate body. The substrate may comprise a combination of more than one type of natural and/or synthetic fibers, such as polypropylene, polyester, viscose, cotton, cellulose, cellulose derivatives, or mixtures thereof. In other embodiments the substrate could comprise a single fiber type. The fibers are formed into non-woven, woven or knitted fabric by various technologies know to those skilled in the art, such as spun bonding, spun lacing, card and bonding, and the like. The substrates have a first surface, a second surface opposite the first surface, and a body disposed between and defined by the first and second surfaces. Examples of fibrous substrates that may be used in gel-wipes according to the invention may include embossed spunlace (8 wave), available from Jacob Holm Industries SAS (Soultz France), or SAWATEX® SPUNLACED NONWOVENS 20068WW51, available from Sandler (Schwartzbach S Germany), or an embossed spunlace non-woven material made from a mixture of 20% Rayon 1.7dtex, 40% Polyester (PET) 1.3dtex and 40% Polyester (PET) 1.7dtex, and has a basis weight of 52 g/m$^2$ available from VAPORJET Ltd Nonwoven Spunlace Industries; (Ofakim, Isreal). Typically, the substrates will have a thickness ranging from about 100 to about 2,000 microns, preferably from about 200 to 1,000 microns.

Many of these substrates utilize thermal bonding to provide the required mechanical resistance between the fibers used to form the substrate. In some instances, the strength of the fabric is further enhanced by the addition of a binder, such as a latex emulsion or solution polymer, to provide a chemical bond between the fibers of the substrate.

As used herein, the term "gelling polymer" means a polymer suitable for and capable of forming a polymeric gel when contacted with an appropriate gelling agent in amounts and under conditions effective to form the polymeric gel. Suitable gelling polymers include both natural and synthetic polymers. Examples of gelling polymers include, but are not limited to, sodium alginate, carboxymethylcellulose, guar gum, guar gum derivatives, e.g. hydroxyethyl guar, carboxymethyl guar, methyl guar, hydroxypropylmethyl guar, cationic guar, cationic hydrophobically modified guar, anionic hydrophobically modified guar, hydrophobically modified guar, borax, pectin gum, carrageenan gum, polyvinyl alcohol, cross linked polyacrylic acid, xanthan gum, gellan gum and ionic polymer or surfactant having a charge, and any combination thereof. The gelling polymer is preferably to be present in an aqueous phase gelling solution at a concentration between about 0.05 to about 5 weight percent, preferably between about 0.10 to about 2 weight percent.

As used herein, the term "gelling agents" means compounds capable of reacting with gelling polymers to form a polymeric gel distributed throughout the substrate when contacted with the gelling polymer in amounts and under conditions effective to form the polymeric gel. Suitable gelling agents include, but are not limited to, $Ca^{2+}$ containing salts; $Al^{3+}$ containing salts; $K^+$ containing salts; borax; neutralizing base solution of cross linked polyacrylic acid; divalent cations of xanthan gum, guar gum, and gellan gum; and polymers or surfactants with an opposite charge of the ionic polymer or surfactant having a charge.

The gelling polymers and the gelling agents may be applied to the substrate sequentially, where the gelling polymer is incorporated with the substrate first, such that the gelling polymer solution is distributed on the first and second surfaces and throughout the body of the substrate and inner core of a substantial portion of the fibers. The gelling agent is then applied to the substrate containing the gelling polymer solution to initiate the polymer gelling reaction, thereby forming a polymeric gel, preferably substantially homogeneously distributed throughout the substrate and inner core of a substantial portion of the fibers.

The gelling polymer may be applied to the substrate by any means known in the art, including, dip tanks, sprays, transfer rollers and the like. Similarly, the gelling agent may be applied to the substrate by any of the above-mentioned means. The amounts of the gelling polymer and gelling agent, respectively, as well as the conditions effective to form the polymeric gel are readily ascertained by those skilled in the art. Methods of removing excess solution from substrates also are known to those skilled in the art. For example, removal of excess solution utilizing pressure and rollers is one example of pressing excess solution from a substrate. Particular conditions of removal of excess solution will be readily ascertainable in view of the specification.

As used herein, the term "polymeric gel" refers to a composition formed by combining a gelling polymer with a gelling agent, each as defined herein, in amounts and under conditions effective to form the polymeric gel, for example, by reaction of the gelling polymer and agent, e.g. by crosslinking, while the composition containing the gelling polymer is in contact with the substrate. In gel-wipes of the present invention, since the substrate has been saturated with the gelling polymer prior to introduction of the gelling agent to the gelling polymer, the polymeric gel is distributed, preferably substantially homogeneously, throughout the body of the substrate, and throughout the inner core of a substantial portion of fibers. As used herein, the term "substantial portion of fibers" means greater than 50 weight percent of fibers in the substrate. In certain embodiments, the substantial portion of fibers having the polymeric gel distributed there through is at least 75 weight percent, or at least 90 weight percent, or at least 95 weight percent, based on the total weight of fiber content in the substrate. It is preferred to have as large a portion of fibers having their inner cores saturated with the polymeric gel as possible, so as to maximize occupation by the polymeric gel of open area and pores within the fibers, as well as the interstitial spaces of the substrate body.

As used herein, the term "liquid cleansing composition" refers to a cleansing composition which provides the desired cleansing properties to the gel-wipe. The liquid cleansing composition may include, but is not limited to, water, emollients, detergents, surfactants, fragrances, preservatives, chelating agents, pH buffers, cleansing agents, or combinations thereof, as all are well known to those skilled in the art. The gel-wipe may contain the liquid cleansing composition in an amount of from about 2 to about 50%, or from about 4 to about 35%, and or about 4 to about 25%.

The liquid cleansing composition suitable for use in gel-wipes of the present invention may be a water-based formulation, in particular an aqueous solution. The composition may be emulsion-based, in which the emulsion can be water-in-oil or oil-in-water, or can be of more complex nature such as water-in-oil-in-water, or oil-in-water-in-oil or a self-organizing liquid crystalline emulsion. The composition also may include Pickering emulsions, micro-emulsions, oil-based solutions or formulations, and hydrodispersions. In one embodiment, the liquid cleansing composition is an oil-in-water emulsion. In another embodiment, the liquid cleaning composition is an oil-in-water emulsion prepared according to the phase inversion technique as known by those skilled in the art. In other embodiments the liquid cleansing composition may be a suspension or slurry that not only cleanses the body, but also soothes and heals the body, especially in babies and in the instance of compromised skin conditions.

Other ingredients that optionally can be included in the liquid cleansing compositions include, without limitation, stabilizers, water thickeners (such as cellulose ethers), oil phase thickeners and stabilizers, suspending agents, colorants, and other benefiting agents. Examples of benefiting agents include oil and fat and their derivatives, conditioning agents, soothing agents, healing agents, insect repellent agents, deodorizing agents, antibiotics, lubricants, luminance, vitamins, moisturizers, softening agents, antistatic agents, static agents, and mixtures thereof.

In certain embodiments of the invention, it was discovered that the cleansing efficacy of the gel-wipes could be significantly improved when the Liquid Cleansing Composition (LCC) applied to the substrate comprising the polymeric gel distributed throughout a substantial portion of the inner core of the fibers was free of a gelling polymer, e.g. Carbomer.

The liquid cleansing compositions of this invention may be formulated into a wide variety of personal care and household cleansing applications, including but not limited to liquid cleansers, creamy cleansers, gel cleansers, soaps, sanitizers and makeup removers.

The liquid cleansing compositions of the invention may contain a carrier, which should be a cosmetically and/or pharmaceutically acceptable carrier. The carrier should be suitable for topical application to the skin, should have good aesthetic properties and should be compatible with other components in the composition. These compositions may comprise several types of cosmetically acceptable topical carriers including, but not limited to, solutions, emulsions (e.g., microemulsions and nanoemulsions), gels, solids and liposomes.

The gel-wipes of the present invention can substantially reduce friction and retain moisture, while providing a soft, soothing and gentle skin cleansing experience. Further, such gel-wipes minimize the amount of liquid cleansing solution, and thus cleansing surfactant, deposited on the gel-wipe substrate and therefore reduces irritation and improves its mildness, while achieving superior cleansing efficacy. In addition, such gel-wipes are more cost effective compared to known gel-wipes, which distribute the cleansing solution and gelling polymer throughout the substrate, including the inner core of the fibers, prior to introduction of the gelling agent to form the polymeric gel. As such, the major portion of cleansing solution trapped by and locked within the inner core of the fibers is isolated from the surface to be cleaned and thus not able to contribute to cleansing, i.e., it is wasted. Gel-wipes of the present invention have utility as personal care wipes, such as baby wipes, cosmetic/facial wipes, wet toilet tissue, adult wipes, sanitizing wipes, intimate feminine care, personal cleansing, nail polish removers and hair remover pull strips.

Figure 2:
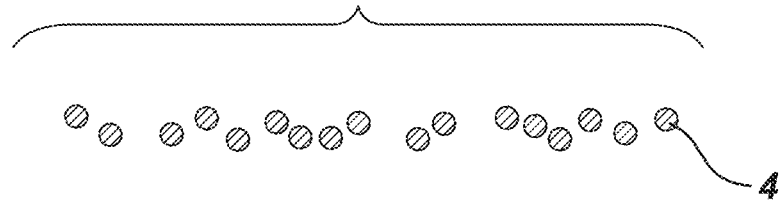
FIG. 2 is a cross-sectional view of the substrate of FIG. 1 taken along line 2.

As seen in the Figures, FIG. 1 is a top view of a substrate used in gel-wipes of the present invention prior to formation of polymeric gel or addition of liquid cleansing composition. The substrate includes fibers 4 and interstitial spaces 6 between the respective fibers used to form the substrate. FIG. 2 is a cross-sectional view of FIG. 1 taken along line 2. As shown in the cross-sectional view, individual fibers 4 do not contain polymeric gel or liquid cleansing solution distributed through their cores.

Figure 3:
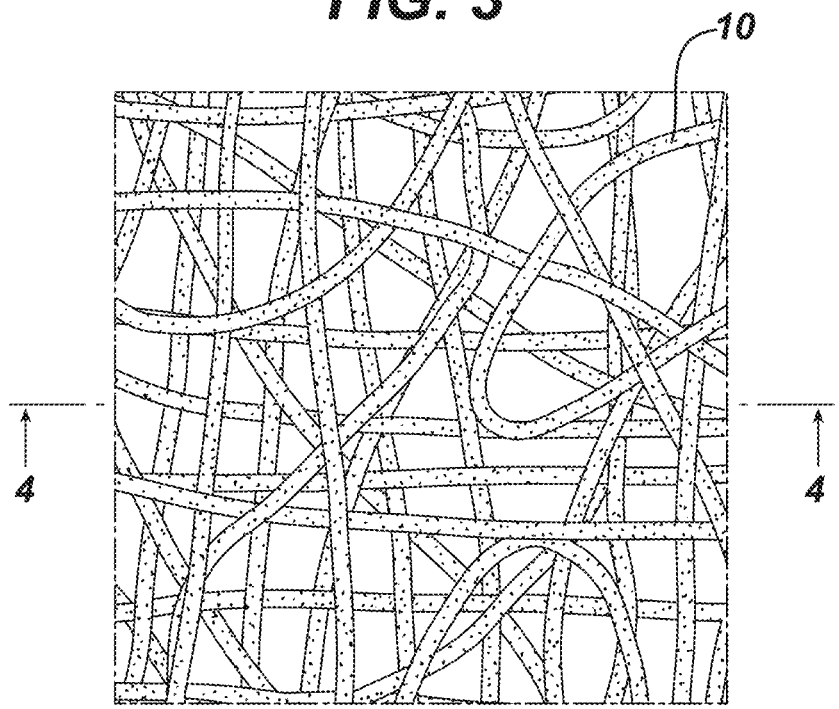
FIG. 3 is a top view of a gel-wipe according to the present invention.
Figure 4:
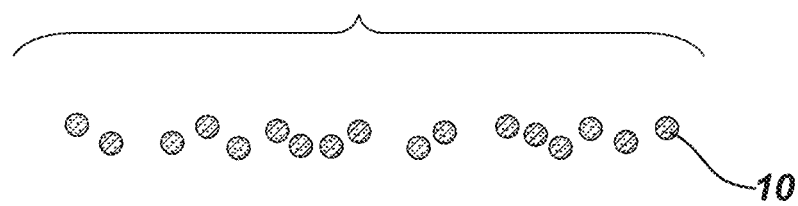
FIG. 4 is a cross-sectional view of the gel-wipe of FIG. 2 taken along line 4.

FIG. 3 is a top view of a gel-wipe after formation of the polymeric gel in the substrate, but prior to application of the liquid cleansing solution. As shown, the stippling indicates the presence of polymeric gel on and throughout the inner core of fibers 10. FIG. 4 is a cross-sectional view of FIG. 3 taken along line 4. As shown in the cross-sectional view, individual fibers 10 contain polymeric gel distributed throughout their cores.

Figure 5:
FIG. 5 is a digital color image of a top view of a gel-wipe according to the present invention.
Figure 6A:
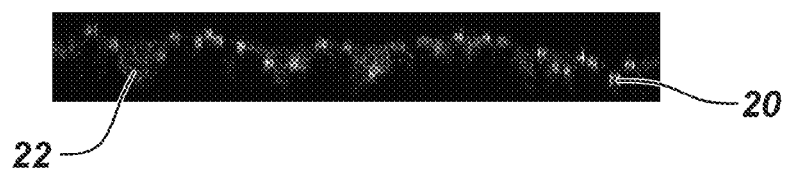
FIG. 6A is a digital color image of a cross-sectional view of FIG. 5 taken along line 6A.
Figure 6B:
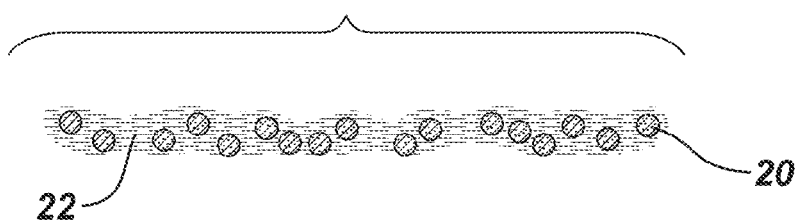
FIG. 6B is a cross-sectional line drawing rendition of FIG. 6A.

FIG. 5 is a digital color image of a top view of a gel-wipe according to the present invention, prepared according to the methods disclosed herein below. As indicated herein below, red indicates the presence of the polymeric gel, while blue indicates the presence of the liquid cleansing composition (J1 in Table 1.1). As shown in FIG. 5, liquid cleansing composition 22 may occupy a portion of the interstitial spaces within the substrate and will adhere to the surfaces of a portion of fibers 20. However, as shown in the digital color image cross-sectional view of FIG. 6A, the inner core of a substantial portion of individual fibers 20 are substantially saturated with polymeric gel and substantially free of the liquid cleansing composition. FIG. 6B is a line drawing rendition of FIG. 6A and shows the inner cores of fibers 20 to be substantially free of liquid cleansing composition 22.

Figure 7:
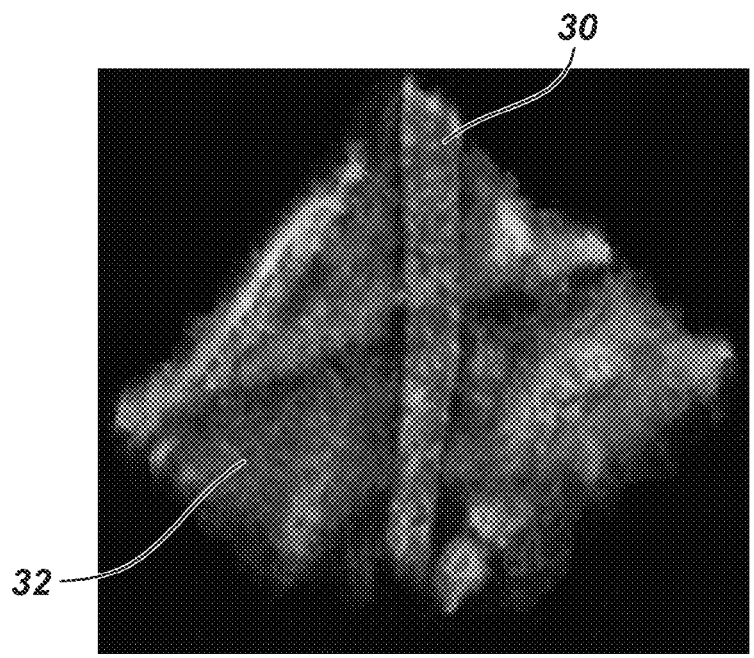
FIG. 7 is digital color image of a bottom view a gel-wipe according to the present invention.
Figure 8:
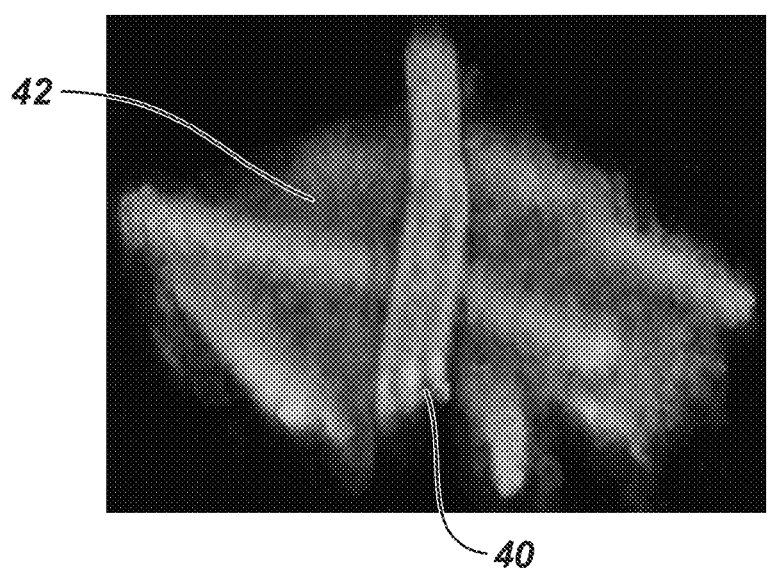
FIG. 8 is a digital color image of a top view of a gel-wipe according to the present invention.

FIG. 7 is a digital color image of a bottom view of a gel-wipe according to the present invention. FIG. 8 is a digital color image of a top view of a gel-wipe according to the present invention. As shown, the gel-wipe includes fibers 30, 42 and liquid cleansing composition 32, 42. As can be seen, fibers 30, 40 are red, indicating that the fibers are coated and saturated with the polymeric gel. A portion of fibers 30, 40 are coated with liquid cleansing composition 32, 42.

The process sequence is critical to providing the novel gel-wipe structure of the present invention that provide superior cleansing efficacy and aesthetic attributes.

A fibrous substrate as described herein is first provided. The fibers comprise an outer surface and an inner core. The substrate comprises a first surface, a second surface opposite the first surface, and a body disposed between and defined by the first and second surfaces. The surfaces may be irregular due to the irregular surfaces of the fibers comprising the substrate.

The substrate is then contacted with a low viscosity composition, e.g., a solution, having a gelling polymer dissolved therein, in amounts and under conditions effective to distribute the solution on the first and second surfaces of the substrate, throughout the body of the substrate, and throughout the inner core of a substantial portion of the fibers. The solution having the gelling polymer dissolved therein is substantially free of the liquid cleaning composition. In certain embodiments, the substrate, including the inner core of the fibers, is saturated with the composition containing the gelling polymer.

Once the composition with the gelling polymer is applied to and distributed throughout the substrate and inner fiber cores, the substrate comprising the gelling polymer distributed there through is contacted with a gelling agent, in amounts and under conditions effective to form the polymeric gel. Thus, a polymeric gel is distributed throughout the substrate, and throughout the inner core of a substantial portion of the fibers.

The substrate comprising the polymeric gel distributed there through is then contacted with a liquid cleansing composition as described herein. As the inner core of the fibers comprises the polymeric gel distributed there through, the inner core of a substantial portion of fibers is substantially free of the liquid cleansing composition. Due to physical attractive forces, not limited to intermolecular Van der Waals forces, the liquid cleansing compositions adhere to and coat the external surfaces of the substrate, including the surface of the fibers. Thus, the liquid cleansing composition is maintained in proximity to the interstitial spaces within the substrate and the external cleaning surface of the gel-wipes. Therefore, the liquid cleansing composition is available for improved cleansing efficacy compared to gel-wipes of the prior art, where the liquid cleansing composition is incorporated into the gelling polymer solution prior to application to the substrate, and thus is bound or locked within the polymeric gel and unavailable for cleansing.

EXAMPLES

The following examples serve to illustrate the invention. While the following examples demonstrate certain embodiments of the invention, they are not to be interpreted as limiting the scope of the invention, but rather as contributing to a complete description of the invention. Parts and percentages are by weight unless otherwise indicated.

Materials Used and Suppliers:

A 0.25% solution of Carbomer 1382 (gelling polymer) was prepared. A 1% solution of NaOH (gelling agent) was prepared. Liquid Cleansing Compositions (LCCs) were also prepared as noted in Tables 1.1, 1.2 and 1.3. Wipe substrates (16 cm×12 cm) were prepared from a Non-woven Fabric (Blend 256), available from Suominen, Finland. To prepare the gel-wipes, 25.0 g each of the 0.25% Carbomer 1382 solution, the 1% NaOH solution, and respective LCCs, were weighed out and placed into separate weighing vessels having a diameter of about 10.5 cm. Each substrate was folded in half prior to the application of any of the gelling polymer or gelling agent solutions, or any LCC.

Vitro-Skin® Testing Substrate Preparation:

Vitro-Skin® with N-19 topography, an advanced testing substrate that mimics the surface properties of human skin, and a plastic hydration chamber with mesh shelves (Complete VITRO-SKIN® N-19 Starter Kit) were obtained from IMS inc., 110 Marginal Way, PMB, Portland Me. (info@ims-usa.com) and used to determine cleaning efficacy of comparative and inventive gel-wipes. First, the 2.5 gallon hydration chamber was prepared. The hydration chamber shelves were removed and all parts of the chamber were washed. 298 grams of purified water and 52 grams of glycerin were added to a clean beaker and were thoroughly mixed. Then, the glycerin-water solution was added to the bottom of the hydration chamber while being careful to not splash on shelves or walls of the chamber. The lid of the hydration chamber was kept on at all times except for when adding or removing the Vitro-Skin® substrate from the chamber.

Revlon® ColorStay Foundation in 450 Mocha for Oily Skin was applied to the Vitro-Skin® substrate prior to hydration. Using a pencil, a circular test area of 2.54 cm (1") diameter was marked on the rough side of the un-hydrated Vitro-Skin substrate using a stencil. As many test areas as necessary were marked, leaving at least one centimeter between each test area. A positive displacement pipette was used to consistently expel and deposit 0.01 mL of foundation to the middle of the marked circular test area. The foundation was spread evenly around the circle, staying within the lines of the circle. The foundation was then left to air dry for about 20 minutes. This procedure was repeated for all test areas. After all test areas had air-dried, the Vitro-Skin® substrate containing the foundation was placed on the shelves in the hydration chamber. The lid of the hydration chamber was closed and the treated Vitro-Skin® substrate was allowed to hydrate for 12-24 hours.

Makeup Removal Process:

A 200 gram weight with a flat bottom was attached onto the rotation end of the Neutrogena WAVE® Sonic 2-speed spinning power-cleanser device where the lower speed was used for all applications. A circular piece of Velcro was then attached to the bottom of the weight.

The treated Vitro-Skin® substrate was removed from the hydration chamber and cut into smaller samples. The smaller sample of Vitro-Skin® was taped securely to a flat surface. The substrate was cut into square 1.5 inch×1.5 inch pieces. One piece of substrate was attached to the Velcro at the bottom of the power-cleanser device. The device was turned on and adjusted by selecting the lower of the two spinning speed options. Next, the rotating end with the wipe was applied to the foundation circle sample and held in place for 10 seconds. After 10 seconds, the device was removed from the foundation test circle and the sample was left to dry for 30 minutes. Each wipe was applied to three foundation test circles with three square pieces of wipe.

Colorimetry:

After 30 minutes of drying, the color parameters of treated substrate samples were read on the Hunter LabScan XE Spectrophotometer (HunterLab, Reston, Va.). The Hunter LabScan XE Spectrophotometer was calibrated and standardized prior to reading each sample. Samples were placed on the Spectrophotometer with the makeup coated side up and the samples were read in the middle of the test circle. The white block was placed over the sample. Samples were read three times in the same spot and these readings were averaged so that each sample had one set of L*a*b values. After all samples had been read, a sample of stained Vitro-Skin (applied makeup without removal) and a sample of unstained Vitro-Skin (Vitro-Skin with no makeup applied) were read using the same process. After all samples had been read, the differences in color were calculated by taking the absolute value of the difference between the sample L, a, or b value and the stained standard L, a, or b value (dL, da, db). Next, the differences were combined to make a quantitative value between the two colors (dE). dE is represented by: $dE=\sqrt{dL^2+da^2+db^2}$. After dE is calculated for each sample, including the unstained sample, the percentage cleansing can be calculated by:

$$\% \text{ Cleansing} = \left(\frac{dE_{Sample}}{dE^{**}_{un\text{-}stained}}\right)*100.$$

Preparation of Digital Color Images:

The following is a description of the methods used to obtain digital color images of FIGS. 5, 6A, 7 and 8.

Wipes were imaged on a Leica TCS SP5 Confocal upright microscope (Leica Microsystems, Germany). Preparation of the wipe used for Imaging is as follows:

A 1 cm×1 cm section of wipe substrate was cut to be used in the formation of the gel-wipe for imaging. 20 µl of 600 µM Rhodamine 123 in water (Invitrogen) was added to 25 grams of a solution of 0.25% Carbomer. 20 µl of 600 µM Rhodamine 800 in water (Sigma-Aldrich) was added to the Liquid Cleansing Composition (LCC-J1) as described in Table 1.1. First, the wipe substrate was submerged in the 0.25% Carbomer solution with Rhodamine 123 for one minute. After the submersion, the wipe substrate was removed and submerged in a 1% NaOH solution for one minute. Then, the wipe was positioned on to a microscope slide and placed in the confocal microscope. The microscope focal positioning was adjusted to find a z-stack range that included both the top of the wipe and the deepest possible fluorescent signal. After the microscope was focused, a drop of the Liquid Cleansing Composition with Rhodamine 800 was dropped onto the wipe and immediately imaged.

A 10× magnification lens was used for the z-stack imaging. The Rhodamine 123 was excited by the 488-nm argon laser and the Rhodamine 800 was excited by the 633-nm He—Ne laser. Each stain was detected at its respective peak emission without crossover. Images were taken at every 1 µm to form the z-stack. Afterwards, the images were analyzed with Volocity.

The confocal microscopy images provide clear evidence of the dual phases of the gel-wipe, i.e. polymeric gel saturated throughout the inner core of fibers (as shown in red) which is substantially free of the liquid cleansing composition and the liquid cleansing composition (J1) surrounding the gel matrix (blue). A cross-sectional view of the images also indicate substantially no liquid cleansing composition penetration into the inner core of the fibers saturated with the polymeric gel.

Example 1

Liquid Cleansing Compositions

The liquid cleansing solution (J1) set forth in Table 1.1 was prepared as follows:

Premix 1: Hexylene Glycol and Tegosoft LSE 65K Soft were mixed in a beaker. Then, Glycerox 767, Dermol SP, Dermol SP, Phenoxyethanol and Euxyl K 702 were added to the mixture with continuous mixing for 40 to 45 minutes at room temperature.

Premix 2: In a separate beaker, DUB INN, DUB PTO and Tegosoft CO, Genapol and Dibetaine were mixed for 30-35 minutes at room temperature. Then, DC fluid was added and mixed for 12-15 minutes at room temperature. Finally, Nipaguard IPF was added and mixed for 20 minutes at room temperature.

Main Phase: In a third beaker, purified water and Carbomer were mixed for 25-30 minutes until dissolved.

Premix 1 was combined with the main phase and mixed for 12-15 minutes. Then, premix 2 was added to the mixture as mixed for another 12-15 minutes at room temperature. The pH was adjusted between 5-6 using 20% NaOH solution.

TABLE 1.1

Liquid Cleaning Composition (J1)

| Trade name | INCI name | w/w % |
| --- | --- | --- |
| Purified Water | Water | 81.67 |
| Carbopol Ultrez 10 | Carbomer | 0 |
| Feverfew | *Chrysanthemum* Extract | 0 |
| Hexylene Glycol | Hexylene Glycol | 1 |
| Genapol EP 2584 | Genapol EP 2584 | 2 |
| Dibetaine UB 3544 | Dibetaine UB 3544 | 2 |
| Meadow Mist | Fragrance | 0 |
| Tegosoft LSE 65K Soft | Sucrose Cocoate | 0.75 |
| Glycerox 767 LQ MH ET42132 | PEG-6 Caprylic/Capric Glycerides | 0.75 |
| Dermol ISP | Isostearyl Palmitate | 2 |
| Phenoxetol | Phenoxyethanol | 0.4 |
| Euxyl K 702 | Ethylhexylglycerin; Dehydroacetic Acid; Benzoic Acid; Phenoxyethanol; | 0.3 |
| Wickenol 151/DUB INN | Isononyl Isononanoate | 2.5 |
| DUB PTO (14150) | Pentaerythrityl Tetraethylhexanoate; Water; 2-Ethyl Hexanoic Acid | 2.5 |
| Tegosoft CO | Cetyl Ethylhexanoate | 2 |
| Xiameter PMX-0245 | Cyclopentasiloxane | 2 |
| Nipaguard IPF | PEG-4 Laurate; Iodopropynyl Butylcarbamate | 0.09 |
| Actiphyte of Aloe Vera 10 Fold GL | *Aloe Barbadensis* Leaf Extract; Glycerin; Water | 0 |
| Actiphyte of Cucumber GL 315912-13 | *Cucumis Sativus* (Cucumber) Fruit Extract; Water; Glycerin | 0 |
| Sodium Hydroxide | Sodium Hydroxide | * 0.04 * QS |
| TOTAL | | 99.96 |

Method for Formulating Liquid Cleansing Composition (J2)

Premix 1: Hexylene glycol and Tegasoft LSE 65K soft were mixed in a beaker. Then, Glycerox 767, Dermol ISP, phenoxyethanol and Euxyl K 702 were added to the mixture with continuous mixing for 40 to 45 minutes at room temperature.

Premix 2: In a separate beaker, DUB PTO and Tegasoft CO were mixed for 30-35 minutes at room temperature. Then, cyclopentasiloxane fluid, Nipaguard IPF, aloe, and cucumber were added and mixed for 20 minutes at room temperature.

Main Phase: In a third beaker, purified water and Carbomer were mixed for 25-30 minutes until dissolved. Feverfew was then added.

Premix 1 was combined with the main phase and mixed for 12 to 13 minutes. Then, premix 2 was added to the mixture and mixed for another 12 to 13 minutes at room temperature. Purified water and NaOH were mixed for 10 minutes, and then added to the mixture of Premix1, Premix 2 and the main phase. Genapol EP 2584 was then added.

Method for Formulating Liquid Cleansing Composition (J3)

Premix 1: Hexylene glycol and Tegasoft LSE 65K soft were mixed in a beaker. Then, Glycerox 767, Dermol ISP, phenoxyethanol and Euxyl K 702 were added to the mixture with continuous mixing for 40 to 45 minutes at room temperature.

Premix 2: In a separate beaker, DUB PTO and Tegasoft CO were mixed for 30-35 minutes at room temperature. Then, cyclopentasiloxane fluid, Nipaguard IPF, aloe, and cucumber were added and mixed for 20 minutes at room temperature.

Main Phase: In a third beaker, purified water was added and mixing initiated. Feverfew was then added.

Premix 1 was combined with the main phase and mixed for 12 to 13 minutes. Then, premix 2 was added to the mixture and mixed for another 12 to 13 minutes at room temperature. Purified water and NaOH were mixed for 10 minutes, and then added to the mixture of Premix1, Premix 2 and the main phase.

Method for Formulating Liquid Cleansing Composition (J0)

Premix 1: In a beaker add hexylene glyceol and tegasoft LSE 65K soft and begin mixing. Continue mixing then add glycerox 767, dermal SP, phenoxy ethanol and Euxyl K 702. Mix for 40 to 45 minutes at room temperature.

Premix 2: In a separate beaker while mixing, add DUB PTO and tegasoft CO. Mix for 30-35 minutes at room temperature. Add cyclo penta siloxane fluid, nipaguard IPF, aloe, cucumber. Mix for 20 minutes at room temperature.

Main Phase: Add purified water and began mixing, add Carbomer, mix for 25-30 mins until dissolved, add feverfew.

Add premix 1 to the main phase and mixed for 12 to 13 mins. Add premix 2 to the main beaker and mix for another 12 to 13 minutes at room temperature. In a separate beaker add purified water and NaOH and mix for 10 minutes and add the solution to the main phase.

TABLE 1.2

Liquid Cleaning Compositions (J2, J3 and J0)

| Trade Name | INCI name | LCC (J0) *w/w % | LCC (J2) *w/w % | LCC (J3) *w/w % |
| --- | --- | --- | --- | --- |
| Purified Water | Water | 85.104 | 83.104 | 83.354 |
| Xiameter PMX-0245 Cyclopentasiloxane 4021402 | Cyclopentasiloxane | 2.00 | 2.00 | 2.00 |
| Glycerox 767 LQ MH ET42132 | PEG-6 Caprylic/Capric Glycerides | 0.75 | 0.75 | 0.75 |
| Phenoxetol | Phenoxyethanol | 0.40 | 0.40 | 0.40 |
| Sodium Hydroxide | Sodium Hydroxide | 0.036 | 0.036 | 0.036 |
| Carbopol Ultrez 10 | Carbomer | 0.25 | 0.25 | |
| Hexylene Glycol | Hexylene Glycol | 1.00 | 1.00 | 1.00 |
| Wickenol 151 | Isononyl Isononanoate | 2.50 | 2.50 | 2.50 |
| Actuohyte of Cucumber GL 315912-13 | *Cucumis Sativus* Fruit Extract, Water, Glycerin | 0.01 | 0.01 | 0.01 |
| Actiphyte of Aloe Vera 10 Fold GL | *Aloe Barbadensis* Leaf Extract, Glycerin, Water | 0.01 | 0.01 | 0.01 |
| DUB PTO (14150) | Pentaerythrityl Tetraethylhexanoate, Water, 2-Ethyl Hexanoic Acid | 2.50 | 2.50 | 2.50 |
| Tegosoft CO | Cetyl Ethylhexanoate | 2.00 | 2.00 | 2.00 |
| Dermol ISP | Isostearyl Palmitate | 2.00 | 2.00 | 2.00 |
| Tegosoft LSE 65K Soft | Sucrose Cocoate | 0.75 | 0.75 | 0.75 |
| Euxyl K 702 | Ethylhexylglycerin, Dehydroacetic Acid, Benzxoic Acid, Phenoxyethanol, Polyaminopropyl Biguanide | 0.30 | 0.30 | 0.30 |
| Nipagard IPF | PEG-4 Laurate, Iodopropynyl Butylcarbamate | 0.09 | 0.09 | 0.09 |
| Feverfew Conc. Enriched Serum Fraction CMP-01A | *Chrysanthemum Parthenium* (Feverfew) Flower/Leaf/Stem Juice | 0.10 | 0.10 | 0.10 |
| Genapol EP 2584 | C12-15 fatty alcohol EO-PO adduct | — | 2.00 | |

*expressed in % w/w

Table 1.3 Liquid Cleaning Composition (J4 Through J7)

The liquid cleansing solutions compositions (J4 through J7) set forth in Table 1.3 were prepared as follows:

Premix 1: Carbomer, Tegosoft CT and Tegosoft LSE 65K Soft were mixed with water in a beaker.

Premix 2: In a separate beaker, Vegelight 1214 LC and chlorophensin were mixed until all ingredients were dissolved.

Premix 2 was then added to Premix 1 and the combination was adjusted to pH 5.5-6.0 with NaOH.

TABLE 1.3

Liquid Cleansing Compositions (J4, J5, J6, and J7)

| Trade Name | INCI Name | LCC (J4) % w/w | LCC (J5) % w/w | LCC (J6) % w/w | LCC (J7) % w/w |
| --- | --- | --- | --- | --- | --- |
| Purified Water | Water | 88.1 | 88.27 | 87.75 | 87.92 |
| Carbopol Ultrez 10 | Carbomer | 0.17 | | 0.17 | |

TABLE 1.3-continued

Liquid Cleansing Compositions (J4, J5, J6, and J7)

| Trade Name | INCI Name | LCC (J4) % w/w | LCC (J5) % w/w | LCC (J6) % w/w | LCC (J7) % w/w |
|---|---|---|---|---|---|
| Tegosoft CT | Caprylic/Capric Triglycerides | 0.75 | 0.75 | 0.75 | 0.75 |
| Tegosoft LSE 65K | Sucrose Cocoate | 0.75 | 0.75 | 0.75 | 0.75 |
| Vegelight 1214 | Coconut Alkanes | 10.0 | 10.0 | | |
| Cetiol CC | Dicaprylyl Carbonate | | | 6.0 | 6.0 |
| Zemea | 1,3-Propanediol | | | 2.0 | 2.0 |
| Lexfeel Natural | Heptyl Undecylensate | | | 2.0 | 2.0 |
| Hydromanil H. GL MS | Water, Glycerin, Hydrolyzxed Caesalpinia Spinosa Gum, Cesakpinia Sinosa Gum | | | 0.1 | 0.1 |
| Chlorophensin | Chlorophensin | 0.2 | 0.2 | 0.2 | 0.2 |
| Citrus Cream RW 1625 | Fragrance | | | 0.25 | 0.25 |
| Sodium Hydroxide | Sodium Hydroxide | .03 | .03 | .03 | .03 |

Example 2

Preparation of Comparative Gel-Wipes (C1, C2 and C3)

2A. Comparative Examples C1 and C2

A 0.25% Carbomer (gelling polymer) solution was prepared using Carbopol 1382. A 1% NaOH solution (gelling agent) was prepared using sodium hydroxide. For the comparative gel-wipes (C1 & C2), the Liquid Cleansing Composition (LCC-J1) as described in Table 1.1 was also prepared. The fibrous wipe substrate, a Non-woven Fabric (Blend 256), available from Suominen, was prepared by cutting a 16 cm×12 cm section of dry wipe substrate and folding in half. To create the comparative gel-wipes, 25.0 grams of each solution was measured into large weigh boats. First, the 0.25% Carbomer solution and the Liquid Cleansing System were mixed in a one to one ratio. For the comparative gel-wipe C1, the substrate was first immersed into 25.0 grams of the mixture of the Carbomer solution and the Liquid Cleansing Composition and allowed to be completely submerged for one minute, thereby saturating the substrate with both the gelling polymer solution and the liquid cleansing composition. After the one-minute submersion, the substrate was removed from the solution, folded into fourths, and drained of excess surfactant. After the substrate was drained of excess surfactant, it was then submerged into 25.0 grams of 1% NaOH solution and the process of a one minute submersion and drainage of excess surfactant was repeated. The resulting comparative gel-wipe comprised the polymeric gel and LCC distributed throughout the substrate and inner core of the fibers. Upon completion, the comparative gel-wipe was retained for further testing.

This same process was repeated for the second comparative wipe (C2). However, for the first submersion, the substrate was dipped into 25.0 grams of 0.25% Carbomer solution. Following the submersion and drainage after this step, the substrate was then submerged into 25.0 grams of a solution of a one-to-one combination of 1% NaOH solution and the Liquid Cleansing Composition. Again, the comparative gel-wipe was dipped for one minute and then drained and retained for further testing.

2B. Comparative Example C3

Utilizing similar steps as for C1 and C2 but without pre-mixing of the 0.25% Carbomer solution and the Liquid Cleansing System, to prepare Comparative Example C3 Liquid Cleansing Composition (LCC-J2) was applied to a fibrous substrate by soaking the substrate in the liquid cleansing Composition (J2). The substrate having the J2 LCC applied thereto was then immersed in a solution of Carbomer (gelling polymer) and then followed by the NaOH (gelling agent).

In view of the fact that all comparative examples combined both the LCC and the gelling polymer in the substrate prior to formation of the polymeric gel by contact of the gelling polymer with the gelling agent, all comparative examples comprise a significant portion of the LCC bound within the inner core of the fibers by the polymeric gel distributed there through.

Example 3

Preparation of Inventive Gel-Wipes (E1 Through E8)

First, fibrous substrates were immersed into 25 grams of a 0.25% Carbomer solution. Once the substrate was completely submerged, the wipe substrate was left in solution for one minute to saturate the substrate with the Carbomer solution. After the submersion, the wipe was removed from the Carbomer solution, folded into fourths (longitudinally) and the excess Carbomer was removed from the wipe. For gel-wipes prepared according to the Examples, the wipe was drained from top to bottom using two gloved fingers, squeezing gently so as to remove the excess Carbomer solution and then the wipe is flipped over and once again drained from top to bottom with two fingers. After the wipe was drained of the 0.25% Carbomer solution, the wipe was immersed in 25.0 g of a 1% NaOH solution for 1 minute, after which time it was removed from the solution and excess solution removed using the same drainage process as describe above. The resulting gel-wipe substrate comprised a polymeric gel distributed throughout the substrate and the inner core of a portion of the fibers. Upon completion of the formation of the substrate comprising the polymeric gel, the wipe was immersed for 1 minute in LCC (J1 for E1 and J2 for E2 respectively), after which time it was removed from the solution and excess solution removed via the drainage process described above. The resultant gel-wipe of the present invention so formed comprises the polymeric gel distributed throughout the inner core of the fibers, while the inner core of the fibers are substantially free of the LCC. The LCC applied after formation of the polymeric gel is distributed on the surface of the substrate and adhered to the surface of the fibers comprising the polymeric gel applied thereto and may be distributed through the interstitial spaces between the fibers of the substrate, to the extent the spaces are not already occupied by the polymeric gel. The gel-wipe was folded into fourths and retained in a sealed plastic bag for testing.

Inventive examples E3-E8 were prepared as above, utilizing LCC J0, J3, J4, J5, J6 and J7 for E3 through E8 respectively.

Comparative Examples C1, C2 and Inventive Example E1 were evaluated and compared for cleaning efficacy using the Vitro-Skin® Testing Substrate as described above. Results are presented below.

| Example | Average % Cleansing | Standard Deviation |
| --- | --- | --- |
| C1 | 63.95 | 8.58 |
| C2 | 65.09 | 8.98 |
| E1 | 87.47 | 1.38 |

Comparative Examples C3 and Inventive Example E2 were evaluated and compared for cleaning efficacy using the Vitro-Skin® Testing Substrate as described above. Results are presented below.

| Example | Average % Cleansing | Standard Deviation |
| --- | --- | --- |
| C3 | 35.2 | 5.53 |
| E2 | 80.6 | 4.05 |

The results clearly demonstrate that inventive gel-wipes E1 and E2, where the gelling polymer solution and the inner core of a portion of the fibers are substantially free of the LCC, exhibited significant improvement in cleaning efficacy when compared to comparative gel-wipe examples, where the LCC is incorporated into the gelling polymer system, and thus incorporated into the polymeric gel upon its formation, thereby binding the LCC within the polymeric gel distributed through the inner core of the fibers.

Inventive Examples E3-E8 were evaluated for cleansing efficacy using the Vitro-Skin® Testing Substrate as described above. Results are presented below.

| Example | Average % Cleansing | Standard Deviation |
| --- | --- | --- |
| E3 | 80.5 | 2.7 |
| E4 | 89.0 | 0.3 |
| E5 | 70.4 | 6.9 |
| E6 | 84.7 | 1.5 |
| E7 | 67.5 | 9.0 |
| E8 | 82.6 | 3.5 |

As the results show, in gel-wipes of the present invention where the LCCs that are applied to the fibrous substrate having the polymeric gel already distributed there through are free of gelling polymers, e.g. Carbomer, yield approximately 10-20 percent improvement in cleaning efficacy compared to LCCs that include a gelling polymer therein.

We claim:

1. A gel-wipe suitable for use in personal care and household cleansing applications, said gel-wipe comprising:
    a substrate comprising fibers, said fibers comprising an outer surface and an inner core, said substrate comprising a first surface, a second surface opposing said first surface, and a body disposed between and defined by said first and second surfaces, said substrate comprising a polymeric gel distributed throughout said substrate and throughout said inner core of a substantial portion of said fibers; and
    a liquid cleansing composition applied to said substrate in an amount effective to provide improved cleansing efficacy to said gel-wipe, wherein said inner core of said substantial portion of said fibers are substantially free of said liquid cleansing composition.

2. The gel-wipe of claim 1 wherein said substrate is selected from the group consisting of woven, non-woven and knitted fabrics.

3. The gel-wipe of claim 1 wherein said polymeric gel comprises a gelling polymer that has been reacted with a gelling agent to form said polymeric gel.

4. The gel-wipe of claim 3 wherein said gelling polymer is selected from the group consisting of sodium alginate, carboxymethylcellulose, guar gum and derivatives thereof, hydroxyethyl guar, carboxymethyl guar, methylguar, hydroxypropylmethyl guar, cationic guar, cationic hydrophobically modified guar, anionic hydrophobically modified guar, hydrophobically modified guar and borax; pectin gum, carrageenan gum; polyvinyl alcohol, cross linked polyacrylic acid, xanthan gum, gellan gum and ionic polymer or surfactant having a charge.

5. The gel-wipe of claim 1 wherein said polymeric gel comprises a cross linked polyacrylic acid.

6. The gel-wipe of claim 3 wherein said gelling agent is selected from the group consisting of $Ca^{2+}$-containing salts, $Al^{3+}$containing salts, $K^+$containing salts; borax; neutralizing base solution of cross linked polyacrylic acid; divalent cations of xanthan gum, guar gum, and gellan gum, polymer or surfactant with an opposite charge of the ionic polymer or surfactant having a charge.

7. The gel-wipe of claim 6 wherein said gelling agent is a neutralizing base solution of cross linked polyacrylic acid.

8. The gel-wipe of claim 6 wherein said gelling agent is sodium hydroxide.

9. The gel-wipe of claim 1 wherein said liquid cleansing composition is substantially free of said polymeric gel.

10. The gel-wipe of claim 1 comprising from about 2 percent to about 50 percent of said liquid cleansing composition.

11. The gel-wipe of claim 1 comprising from about 4 percent to about 35 percent of said liquid cleansing composition.

12. The gel-wipe of claim 1 comprising from about 0.05 percent to about 5 percent by weight of said polymeric gel.

13. The gel-wipe of claim 1 wherein said substantial portion of fibers comprises at least 75 percent by weight of said fibers.

14. The gel-wipe of claim 1 wherein said substantial portion of fibers comprises at least 90 percent by weight of said fibers.

15. The gel-wipe of claim 1 wherein said polymeric gel is substantially free of said liquid cleansing composition.

16. The gel-wipe of claim 1 wherein said liquid cleansing composition is substantially free of a gelling polymer.

17. A method of making a gel-wipe suitable for use in personal care and household cleansing applications, the method comprising the ordered steps of:
    providing a substrate comprising fibers, said fibers comprising an outer surface and an inner core, said substrate comprising a first surface, a second surface opposing said first surface, and a body disposed between and defined by said first and second surfaces;
    contacting said substrate with a solution having a gelling polymer dissolved therein, under conditions effective to distribute said solution on said first and second surfaces of said substrate, throughout said body of said substrate, and throughout said inner core of a substantial portion of said fibers;

removing excess solution having the gelling polymer dissolved therein from said substrate;

contacting said substrate comprising said gelling polymer distributed there through with a gelling agent capable of providing a polymeric gel comprising said gelling polymer and then removing excess solution having the gelling agent dissolved therein from said substrate, thereby forming said polymeric gel distributed throughout said substrate, and throughout said inner core of said substantial portion of said fibers;

contacting said substrate comprising said polymeric gel distributed there through with a liquid cleansing composition; and removing excess liquid cleansing composition from said substrate comprising said polymeric gel and said liquid cleansing composition; wherein said solution having said gelling polymer dissolved therein is substantially free of said liquid cleaning composition, and wherein said inner core of said substantial portion of fibers comprising said polymeric gel distributed there through is substantially free of said liquid cleansing composition.

* * * * *